United States Patent
Lee et al.

(10) Patent No.: US 11,553,866 B2
(45) Date of Patent: Jan. 17, 2023

(54) NANOFIBER MESH BIOELECTRODE, AND METHOD FOR PRODUCING THE SAME

(71) Applicant: DAEGU GYEONGBUK INSTITUTE OF SCIENCE AND TECHNOLOGY, Daegu (KR)

(72) Inventors: Sung-Won Lee, Chungcheongnam-do (KR); Woo-Seong Jeong, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 373 days.

(21) Appl. No.: 16/837,309

(22) Filed: Apr. 1, 2020

(65) Prior Publication Data

US 2020/0375486 A1 Dec. 3, 2020

(30) Foreign Application Priority Data

Apr. 1, 2019 (KR) .......................... 10-2019-0037849

(51) Int. Cl.
*C08L 67/04* (2006.01)
*A61B 5/24* (2021.01)

(52) U.S. Cl.
CPC ................ *A61B 5/24* (2021.01); *C08L 67/04* (2013.01); *A61B 2562/125* (2013.01); *C08L 2203/12* (2013.01); *C08L 2203/20* (2013.01)

(58) Field of Classification Search
CPC ..... A61B 5/24; A61B 2562/125; C08L 67/04; C08L 2203/12; C08L 2203/20
USPC ....... 528/373, 378, 380; 428/411.1; 600/395
See application file for complete search history.

(56) References Cited

U.S. PATENT DOCUMENTS

| | | | |
|---|---|---|---|
| 10,959,634 B2 * | 3/2021 | Varadan | A61B 5/0022 |
| 2016/0374615 A1 * | 12/2016 | Tsukada | D06M 15/3566 |
| | | | 600/382 |
| 2021/0244304 A1 * | 8/2021 | Park | H01B 1/124 |

FOREIGN PATENT DOCUMENTS

| | | |
|---|---|---|
| KR | 10-2011-0129113 A | 12/2011 |
| KR | 10-2013-0006259 A | 1/2013 |
| KR | 101284373 B1 | 7/2013 |
| KR | 2014-0128528 A | 11/2014 |
| KR | 10-2016-0140260 A | 12/2016 |
| KR | 10-2017-0039828 A | 4/2017 |

OTHER PUBLICATIONS

Korean Office Action for Application No. KR-10-2019-0037849, dated Jul. 30, 2020.
International Search Report dated Sep. 1, 2020 issued in corresponding International Application No. PCT/KR2020/004359.

* cited by examiner

Primary Examiner — Terressa Boykin
(74) Attorney, Agent, or Firm — Harness, Dickey & Pierce, P.L.C.

(57) ABSTRACT

Provided are a nanofiber mesh bioelectrode including: a nanofiber mesh sheet in which nanofibers containing a biocompatible water-soluble polymer are entangled in a network form; and a conductive layer coated on the nanofiber mesh sheet and including a conductive material, and a method of producing the same. The nanofiber mesh bioelectrode according to the present invention does not cause discomfort when applied to a living body due to its excellent biocompatibility and excellent flexibility, and easily measures a biosignal or easily applies stimulation for a long period of time, as the nanofiber mesh bioelectrode is not easily detached.

14 Claims, 3 Drawing Sheets

NANOFIBER MESH BIOELECTRODE, AND METHOD FOR PRODUCING THE SAME

CROSS-REFERENCE TO RELATED APPLICATIONS

This application claims priority under 35 U.S.C. § 119 to Korean Patent Application No. 10-2019-0037849, filed on Apr. 1, 2019, in the Korean Intellectual Property Office, the disclosure of which is incorporated herein by reference in its entirety.

TECHNICAL FIELD

The following disclosure relates to a nanofiber mesh bioelectrode and a method of producing the same.

BACKGROUND

Various microelectrodes for measuring a biosignal have been produced, and most of the microelectrodes have been produced by using a micro-electro mechanical system (MEMS) technique based on silicon.

In a case of a silicon-based electrode which has been developed, measurement characteristics vary and measurement performance is degraded due to progression of gliosis around the electrode caused by reduction of biocompatibility over time. In addition, since fixibility of the electrode is insufficient, the electrode is not easily fixed to a nerve tissue and causes damage to the nerve tissue.

In particular, in a case of an implantable electrode to be connected to artificial eyes, artificial ears, and brain cells, it is very important to have biocompatibility because the implantable electrode needs to be directly connected to a sensitive cell.

In order to solve such problems, bioelectrodes of various types and purposes have been produced using a flexible substrate formed of polyimide, parylene, SU-8, polydimethylsiloxane, or the like.

Among them, polydimethylsiloxane, that is a polymer having flexibility similar to that of a biological tissue, has been widely used as a material for a microfluidic chip because it has transparent material properties and to be easily produced by a soft lithography process.

In particular, polydimethylsiloxane has excellent biocompatibility and excellent permeability to moisture and air, and thus, polydimethylsiloxane is sufficiently useful for an electrode that may measure a biosignal or may apply electrical stimulation in a state of being implanted in a living body for a long period of time.

However, in spite of the excellent biocompatibility of polydimethylsiloxane, in a case where an electrode is formed based on polydimethylsiloxane, a metal layer is difficult to be formed due to differences between materials, such as differences in lattice constants and thermal expansion coefficients between polydimethylsiloxane, which is a silicon-based organic polymer, and the metal layer, and the metal layer and polydimethylsiloxane are easily separated from each other due to a weak adhesive force there between when the metal layer is patterned to have a line width in a micrometer unit.

In addition, in a case of a bioelectrode formed on a flat substrate, permeability to sweat and gas is not good, and an adhesive material needs to be used for adhesion between skin and the bioelectrode, which causes dermatitis. Further, even in a case where a flat substrate having excellent flexibility is used, the flat substrate is not soft compared with skin but is hard, and thus, the flat substrate is easily detached from skin or causes discomfort. Therefore, the bioelectrode formed on a flat substrate has a limitation in monitoring a biosignal while being attached to skin for a long period of time.

Therefore, the present inventors intend to provide a bioelectrode capable of being easily produced while having excellent biocompatibility, excellent permeability to moisture and air, and excellent flexibility similar to that of skin, and a method of producing the same.

Korean Patent Publication No. 10-1284373 is suggested as a similar related art.

RELATED ART DOCUMENT

Patent Document

Korean Patent Publication No. 10-1284373 (Jul. 3, 2013)

SUMMARY

An embodiment of the present invention is directed to providing a bioelectrode capable of being easily produced while having excellent biocompatibility, excellent permeability to moisture and air, and excellent flexibility similar to that of skin, and a method of producing the same.

In one general aspect, a nanofiber mesh bioelectrode includes: a nanofiber mesh sheet in which nanofibers containing a biocompatible water-soluble polymer are entangled in a network form; and a conductive layer coated on the nanofiber mesh sheet and including a conductive material.

The nanofiber mesh bioelectrode may further include a protective layer formed between the nanofiber mesh sheet and the conductive layer and containing a biocompatible hydrophobic polymer. The biocompatible hydrophobic polymer may be one or two or more selected from the group consisting of parylene, polycaprolactone (PCL), polylactic acid (PLA), and a polylactic acid-co-glycolic acid (PLGA) copolymer. A thickness of the protective layer may be 50 to 1,000 nm.

The biocompatible water-soluble polymer may be one or two or more selected from the group consisting of polyvinyl alcohol (PVA), polyethylene glycol (PEG), polypropylene glycol (PPG), polyacrylic acid (PAA), carboxymethyl cellulose (CMC), polyvinylpyrrolidone (PVP), starch, gelatin, hyaluronic acid, chitin, chitosan, alginic acid, dextran, fibrin, heparin, and salts thereof.

A thickness of the nanofiber may be 10 to 990 nm. A thickness of the conductive layer may be 1 to 500 nm.

The nanofiber mesh bioelectrode may be an implantable bioelectrode.

The nanofiber mesh bioelectrode may further include an insulating layer formed on the conductive layer and containing a biocompatible hydrophobic polymer.

The insulating layer may be a patterned insulating layer having a pattern in which the conductive layer is exposed to an upper portion of the insulating layer.

In another general aspect, a method of producing a nanofiber mesh bioelectrode includes: a) producing a nanofiber mesh sheet in which nanofibers containing a biocompatible water-soluble polymer are entangled in a network form by using electrospinning; and b) coating a conductive material on the nanofiber mesh sheet.

The method may further include, before the coating of the conductive material, coating a protective layer containing a biocompatible hydrophobic polymer on the nanofiber mesh sheet. The coating of the protective layer may be performed by a chemical vapor deposition (CVD) method.

In b), the coating may be performed by a sputtering deposition method, a thermal deposition method, an electron-beam deposition method, a chemical vapor deposition (CVD) method, or an atomic layer deposition (ALD) method.

Other features and aspects will be apparent from the following detailed description, the drawings, and the claims.

BRIEF DESCRIPTION OF THE DRAWINGS

FIG. 5B illustrates an enlarged view of a part of a cycle of FIG. 5C.

DETAILED DESCRIPTION OF EMBODIMENTS

Figure 1B:
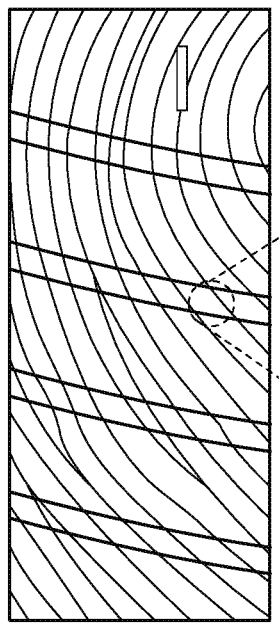
FIG. 1B is an actual photograph of the nanofiber mesh bioelectrode transferred onto the skin.
Figure 1C:
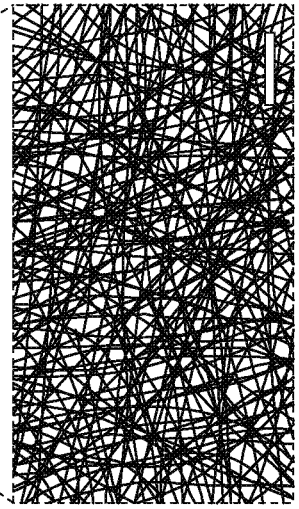
FIG. 1C is an enlarged image of a portion of the mesh bioelectrode transferred onto the skin obtained with a scanning electron microscope (SEM).
Figure 1A:
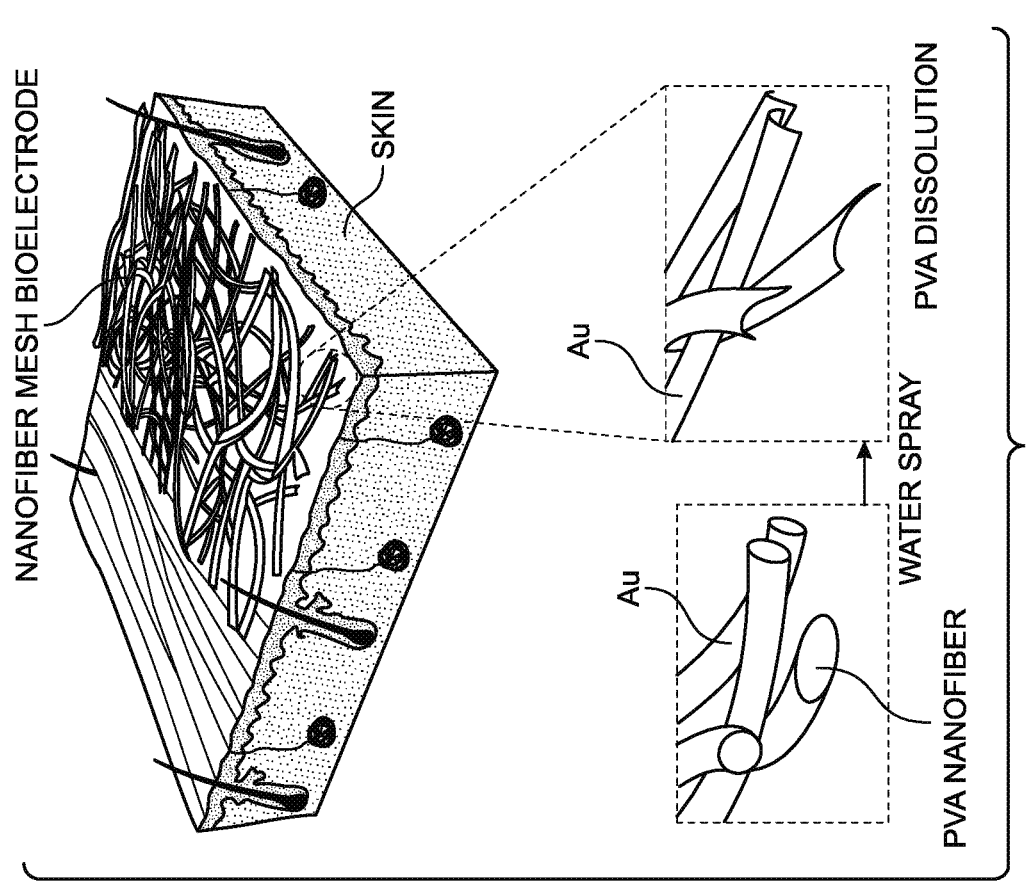
FIG. 1A is a schematic view illustrating a state in which a nanofiber mesh bioelectrode produced according to an exemplary embodiment of the present invention is transferred onto skin.
Figure 2:
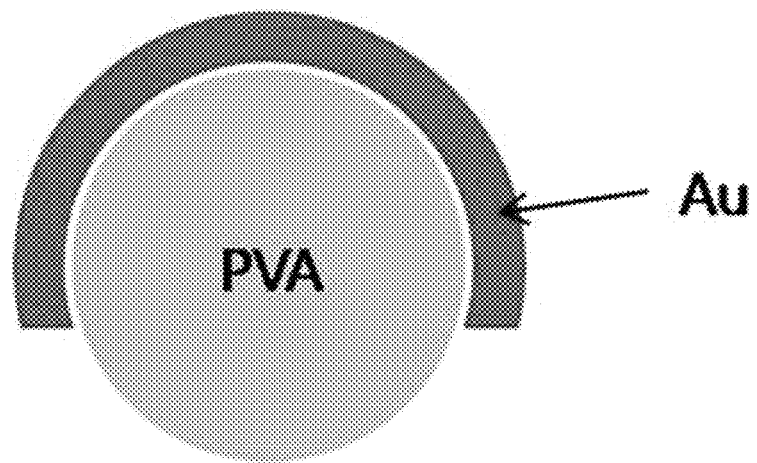
FIG. 2 is a schematic view illustrating a strand of nanofibers constituting a nanofiber mesh bioelectrode produced according to Example 1 of the present invention.
Figure 3:
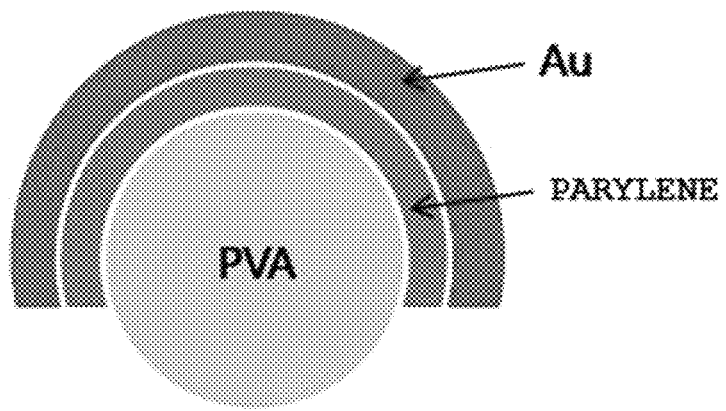
FIG. 3 is a schematic view illustrating a strand of nanofibers constituting a nanofiber mesh bioelectrode produced according to Example 3 of the present invention.

Hereinafter, a nanofiber mesh bioelectrode and a method of producing the same according to the present invention will be described in detail with reference to the accompanying drawings. The drawings to be described below are provided by way of example so that the spirit of the present invention can be sufficiently transferred to those skilled in the art. Therefore, the present invention is not be limited to the drawings suggested below but may be modified in many different forms. In addition, the drawings suggested below will be exaggerated in order to clarify the spirit of the present invention. In addition, the same components are denoted by the same reference numerals throughout the specification.

Technical terms and scientific terms used herein have the general meanings understood by those skilled in the art to which the present invention pertains unless otherwise defined, and a description for the known function and configuration obscuring the present invention will be omitted in the following description and the accompanying drawings.

In addition, the terms "first", "second", "A", "B", "(a)", "(b)", and the like may be used to describe components of the present invention. These terms are only used to distinguish one component from another component, and natures, orders, or sequences of these components are not be limited by these terms.

In addition, the term "biocompatibility" used in the present invention may refer to a characteristic in which rejection such as an inflammation, an allergy, toxicity, a cancer, or thrombus formation does not occur when a biomaterial is in contact with a biological tissue, a body fluid, or the like.

A bioelectrode according to the related art may cause damage to a tissue due to a lack of biocompatibility. In a case of a flat bioelectrode, permeability to sweat and gas is not good, and an adhesive material needs to be used for adhesion between skin and the bioelectrode, which may cause dermatitis. Further, even in a case where a flat substrate having excellent flexibility is used, the flat substrate is not soft compared with skin but is hard, and thus, the flat substrate is easily detached from skin or causes discomfort. Therefore, the flat bioelectrode has a limitation in monitoring a biosignal while being attached to skin for a long period of time.

Accordingly, as a result of extensive studies to solve the above problems, the present inventors found that, in a case where a bioelectrode having a mesh structure in which fiber strands are entangled in a network form is produced, it is possible to provide a bioelectrode having excellent permeability to moisture and air and excellent flexibility similar to that of skin, thereby completing the present invention.

Specifically, the bioelectrode according to the present invention may be a nanofiber mesh bioelectrode including a nanofiber mesh sheet in which nanofibers containing a biocompatible water-soluble polymer are entangled in a network form; and a conductive layer coated on the nanofiber mesh sheet and including a conductive material.

As such, by using a polymer having excellent biocompatibility and a conductive material, the nanofiber mesh bioelectrode according to the present invention may have excellent biocompatibility. Further, by having a nanofiber mesh structure in which fiber strands are entangled in a network form, the nanofiber mesh bioelectrode according to the present invention may have excellent permeability to moisture and air. Therefore, the nanofiber mesh bioelectrode may not cause dermatitis, damage to a nerve tissue, and the like even when the nanofiber mesh bioelectrode is attached to skin or is implanted in a living body for a long period of time.

In addition, the nanofiber mesh bioelectrode according to the present invention has the nanofiber mesh structure in which fiber strands are entangled in a network form, such that the nanofiber mesh bioelectrode may have excellent flexibility similar to that of skin. Therefore, the nanofiber mesh bioelectrode may be easily fixed to skin or a tissue in a living body, and may not be easily detached from the tissue because it is flexibly bent or stretched even when a human body moves. Thus, as the nanofiber mesh bioelectrode is not easily detached from the tissue for a long period of time, the nanofiber mesh bioelectrode may easily measure a biosignal, or may easily apply electrical stimulation for a long period of time.

In addition, since the biocompatible water-soluble polymer serves as an adhesive, the nanofiber mesh bioelectrode may be attached and fixed to skin or a tissue in a living body without a separate adhesive material.

Accordingly, the nanofiber mesh bioelectrode according to an exemplary embodiment of the present invention may be applied as a skin attachable bioelectrode or an implantable bioelectrode.

Specifically, the bioelectrode may measure a biosignal generated from a human body. Alternatively, the bioelectrode may be applied as a biointerface capable of applying stimulation to the human body. For example, the biointerface may be for examining a biosignal such as electrocardiogram (ECG), electromyogram (EMG), or electroencephalogram (EEG).

In addition, the biointerface may apply stimulation to a nerve tissue or to an abnormal tissue (tumor).

Specifically, for example, the biointerface may be a spinal nerve stimulator. Pain felt by a cancer patient is relieved by continuously injecting a painkiller or stimulating a spinal nerve so as to blunt a patient's senses. In this case, in general, the spinal nerve simulation is invasively performed by a needle, which may be very inconvenient. On the other hand, the nanofiber mesh bioelectrode according to an exemplary embodiment of the present invention may be implanted in a spinal nerve, and stimulation may be easily applied to the spinal nerve after the implant, which may improve patient's convenience. In addition, the nanofiber mesh bioelectrode is implanted in an abnormal tissue (tumor) and simulation is applied thereto so as to necrotize the abnormal tissue. As a result, the tumor may be treated.

Hereinafter, respective constituent materials of the nanofiber mesh bioelectrode according to the present invention will be described in more detail.

First, a nanofiber mesh sheet in which nanofibers containing a biocompatible water-soluble polymer are entangled in a network form will be described.

In an exemplary embodiment of the present invention, any biocompatible water-soluble polymer may be used without particular limitation as long as it is a polymer having excellent biocompatibility and water-soluble property. Specifically, for example, the biocompatible water-soluble polymer may be one or two or more selected from the group consisting of polyvinyl alcohol (PVA), polyethylene glycol (PEG), polypropylene glycol (PPG), polyacrylic acid (PAA), carboxymethyl cellulose (CMC), polyvinylpyrrolidone (PVP), starch, gelatin, hyaluronic acid, chitin, chitosan, alginic acid, dextran, fibrin, heparin, and salts thereof.

Preferably, the biocompatible water-soluble polymer according to an exemplary embodiment of the present invention may be polyvinyl alcohol (PVA). Polyvinyl alcohol, which is non-toxic and non-carcinogenic, not only has excellent biocompatibility, but also has easy processability to be easily processed into a desired form.

In an exemplary embodiment of the present invention, any biocompatible water-soluble polymer having a molecular weight at which the polymer may be soluble in water may be used without particular limitation. Specifically, for example, a weight average molecular weight of the biocompatible water-soluble polymer may be 10,000 to 500,000 g/mol, preferably 30,000 to 300,000 g/mol, more preferably 50,000 to 200,000 g/mol, and most preferably 80,000 to 150,000 g/mol.

In an exemplary embodiment of the present invention, a thickness of the nanofiber containing a biocompatible water-soluble polymer may be adjusted depending on a shape of a desired bioelectrode. For example, the thickness of the nanofiber may be preferably 10 to 990 nm, more preferably 300 to 800 nm, and most preferably 400 to 600 nm. Within the above range, the fiber strands are entangled in a network form even after coating of the conductive material so as to form a nanofiber mesh structure. Therefore, the nanofiber mesh electrode may have excellent permeability to moisture and air and excellent flexibility due to the nanofiber mesh structure, and may be easily attached and fixed to skin or a tissue in a living body without a separate adhesive material, as the biocompatible water-soluble polymer is easily soluble in water.

In addition, in an exemplary embodiment of the present invention, a thickness of the nanofiber mesh sheet may be 700 nm to 3 μm, preferably 800 nm to 2 μm, and most preferably 1 μm to 1.5 μm. Within the above range, the nanofiber mesh electrode may have excellent flexibility similar to that of skin and may be easily attached to skin or a tissue in a living body.

Next, the conductive layer containing a conductive material will be described.

In an exemplary embodiment of the present invention, the conductive material allows the nanofiber mesh bioelectrode to act as an electrode. As the conductive material, it is preferable to use a metal having biocompatibility that does not cause rejection or damage to a human body while having excellent conductivity. Specifically, for example, the metal may be gold (Au), platinum (Pt), silver (Ag), or the like, and may be preferably gold (Au).

In an exemplary embodiment of the present invention, the conductive layer containing a conductive material may be coated on the nanofiber mesh sheet, and specifically, may be partially or entirely coated on a region of the nanofiber mesh sheet. Preferably, the conductive layer may be patterned to be partially coated on the region of the nanofiber mesh sheet depending on a desired design. However, as described above, a region to be coated may be selected depending on use and a required structure of the bioelectrode.

In an exemplary embodiment of the present invention, a thickness of the conductive layer containing a conductive material may be adjusted depending on a shape of a desired bioelectrode. For example, the thickness of the conductive layer may be 1 to 500 nm, preferably 5 to 300 nm, and most preferably 10 to 100 nm. Within the above range, the nanofiber mesh electrode may have excellent flexibility similar to that of skin while having excellent conductivity. Therefore, the nanofiber mesh bioelectrode may not be easily detached from a tissue because it is flexibly bent or stretched even when a human body moves. Thus, as the nanofiber mesh bioelectrode is not easily detached from the tissue for a long period of time, the nanofiber mesh bioelectrode may easily measure a biosignal or may easily apply electrical stimulation for a long period of time.

In addition, the nanofiber mesh bioelectrode according to an exemplary embodiment of the present invention may further include a protective layer formed between the nanofiber mesh sheet and the conductive layer and containing a biocompatible hydrophobic polymer.

As such, by forming the protective layer that is insoluble in water between the nanofiber mesh sheet and the conductive layer, the biocompatible water-soluble polymer may not be completely dissolved in water, which may prevent a shape of the nanofiber mesh bioelectrode from being changed greatly. Therefore, damage to the conductive layer caused by a change in shape of the nanofiber mesh bioelectrode may be prevented. In addition, mechanical properties of the nanofiber mesh bioelectrode may be enhanced, which enables the nanofiber mesh bioelectrode to be easily used.

Specifically, when the nanofiber mesh bioelectrode is fixed to skin or a tissue in a living body, adhesion of the nanofiber mesh bioelectrode is performed by partially or entirely dissolving the biocompatible water-soluble polymer through spraying of water. When it is intended to partially dissolve the biocompatible water-soluble polymer so as to maintain the shape of the nanofiber mesh bioelectrode while securing adhesion performance, it is possible to partially dissolve the biocompatible water-soluble polymer by coating a surface of the nanofiber mesh sheet with the protective layer. On the contrary, when it is intended to remove all or almost the biocompatible water-soluble polymer so as to leave only the conductive layer, the protective layer may not be included.

In an exemplary embodiment of the present invention, any polymer may be used as the biocompatible hydrophobic polymer without particular limitation as long as the polymer has excellent biocompatibility and is insoluble in water. Specifically, for example, the biocompatible hydrophobic polymer may be one or two or more selected from the group consisting of parylene, polycaprolactone (PCL), polylactic acid (PLA), and a polylactic acid-co-glycolic acid (PLGA) copolymer. Preferably, the biocompatible hydrophobic polymer may be parylene. Parylene has excellent biocompatibility, and may be coated on the surface of the nanofiber mesh sheet by a deposition method as described below, and thus, a thickness of a parylene layer may be easily adjusted. The protective layer to be coated may have no pinholes and pores because parylene is subjected to vacuum deposition in a form of a gas phase under vacuum. The nanofiber mesh sheet may be stably protected by coating the surface of the nanofiber mesh sheet with parylene due to a very stable molecular structure of parylene.

In an exemplary embodiment of the present invention, a thickness of the protective layer containing a biocompatible hydrophobic polymer may be adjusted depending on a shape of a desired bioelectrode. For example, the thickness of the protective layer may be preferably 50 to 1,000 nm, more preferably 100 to 800 nm, and most preferably 200 to 500 nm. Within the above range, by partially dissolving the biocompatible hydrophobic polymer, the shape of the nanofiber mesh bioelectrode may be maintained while securing adhesion performance, and excellent mechanical properties of the nanofiber mesh bioelectrode may be secured while maintaining flexibility.

In addition, the nanofiber mesh bioelectrode according an exemplary embodiment of the present invention may further include an insulating layer coated on the conductive layer and containing a biocompatible hydrophobic polymer.

As such, the conductive layer may be protected from the outside by forming the insulating layer that is insoluble in water on the conductive layer. In addition, a mechanical strength of the bioelectrode is further enhanced, and thus, it is possible to provide a biointerface that may be more easily used.

Specifically, after the nanofiber mesh bioelectrode is installed in skin or a tissue of a living body, a short circuit in the conductive layer may occur due to moisture inside or outside the tissue, blood, or the like. The insulating layer is coated on the conductive layer, such that it is possible to prevent the short circuit from occurring in the conductive layer due to moisture and blood. In addition, the mechanical strength of the bioelectrode is further enhanced, which may prevent the short circuit from occurring in the conductive layer due to a change in shape of the bioelectrode. As such, the insulating layer protects the conductive layer from the outside and enhances the mechanical strength of the bioelectrode, and thus, it is possible to provide a biointerface that may be further stably used.

Any polymer may be used as the biocompatible hydrophobic polymer without particular limitation as long as the polymer has excellent biocompatibility and is insoluble in water. Specifically, for example, the biocompatible hydrophobic polymer may be one or two or more selected from the group consisting of parylene, polycaprolactone (PCL), polylactic acid (PLA), and a polylactic acid-co-glycolic acid (PLGA) copolymer.

Preferably, any polymer may be used without particular limitation as long as the polymer has excellent biocompatibility and is insoluble in water. Specifically, for example, the biocompatible hydrophobic polymer may be preferably parylene. Parylene has excellent biocompatibility, and may be coated on a surface of the conductive layer by a deposition method as described below, and thus, a thickness of a parylene layer may be easily adjusted. In addition, the protective layer to be coated may have no pinholes and pores because parylene is subjected to vacuum deposition in a form of a gas phase under vacuum. The conductive layer may be stably protected by coating the surface of the conductive layer with parylene due to a very stable molecular structure of parylene.

In an exemplary embodiment of the present invention, the insulating layer may be a patterned insulating layer having a pattern in which the conductive layer is exposed to an upper portion of the insulating layer. The insulating layer may be variously patterned depending on the type of the biointerface to which the bioelectrode is applied. As such, the insulating layer having the pattern in which the conductive layer is exposed to the upper portion of the insulating layer protects the conductive layer and prevents degradation of sensitivity of the conductive layer to stimulation. A pattern may be formed on the insulating layer by coating the insulating layer on the conductive layer and then performing etching through a dry etching process such as a plasma etching process.

In an exemplary embodiment of the present invention, a thickness of the insulating layer may be adjusted depending on a shape of a desired bioelectrode. For example, the thickness of the insulating layer may be preferably 50 to 2,000 nm, more preferably 100 to 1,500 nm, and most preferably 300 to 700 nm. Within the above range, the insulating layer may prevent moisture from being introduced into the conductive layer and may secure excellent mechanical properties of the nanofiber mesh bioelectrode while maintaining flexibility.

In addition, another aspect of the present invention relates to a method of producing a nanofiber mesh bioelectrode. The method of producing a nanofiber mesh bioelectrode according to an exemplary embodiment of the present invention may include: a) producing a nanofiber mesh sheet in which nanofibers containing a biocompatible water-soluble polymer are entangled in a network form by using electrospinning; and b) coating a conductive material on the nanofiber mesh sheet.

The nanofiber mesh bioelectrode is produced by producing the nanofiber mesh sheet in which the nanofibers are entangled in a network form by using electrospinning in advance, and then coating the nanofiber mesh sheet with the conductive material, such that a microelectrode may be relatively easily produced due to easy micromachining.

Hereinafter, each step of the method of producing a nanofiber mesh bioelectrode will be described in detail. However, the types of respective constituent materials and the like are same as those described in the nanofiber mesh bioelectrode. Accordingly, an overlapped description will be omitted.

First, a) producing of a nanofiber mesh sheet in which nanofibers containing a biocompatible water-soluble polymer are entangled in a network form by using electrospinning may be performed.

The electrospinning may be performed by a method typically used in the art. Specifically, when a biocompatible water-soluble polymer aqueous solution was charged into a syringe, and then a high voltage is applied while discharging the aqueous solution through a needle tip, the biocompatible water-soluble polymer aqueous solution which is a liquid phase may be formed into nano-sized fibers through an electric field generated by the high voltage.

More specifically, the biocompatible water-soluble polymer aqueous solution according an exemplary embodiment of the present invention is prepared by dissolving a biocompatible water-soluble polymer in a solvent such as water. A concentration of the biocompatible water-soluble polymer in the biocompatible water-soluble polymer aqueous solution may be 5 to 30 wt %, preferably 8 to 20 wt %, and most preferably 10 to 15 wt %. Within the above range, the nanofibers may be formed into a continuous fiber without being broken into several filaments and fine nanofibers suitable for a bioelectrode may be well produced.

In order to effectively produce the nanofiber mesh sheet, a distance between the needle tip and a collector, an intensity of a voltage, and a discharge rate of the biocompatible water-soluble polymer aqueous solution are important. The distance between the needle tip and the collector according to an exemplary embodiment of the present invention may be 5 to 50 cm, preferably 10 to 40 cm, and most preferably 15 to 30 cm. When the distance is too small, adhesion between the nanofibers may be excessive, and when the distance is too large, it may be difficult to form a continuous fiber due to evaporation of the solvent.

The intensity of the voltage according to an exemplary embodiment of the present invention is not particularly limited as long as it is an intensity of a voltage typically applied to form nanofibers. Specifically, for example, the intensity of the voltage may be 1 to 30 kV, preferably 5 to 25 kV, and more preferably 10 to 20 kV. Within the above range, the electrospinning may be effectively performed.

The discharge rate according to an exemplary embodiment of the present invention is to adjust the thickness of the nanofiber depending on a desired thickness without breakage by adjusting the concentration of the biocompatible water-soluble polymer aqueous solution and the amount of the biocompatible water-soluble polymer aqueous solution to be discharged. Specifically, for example, the discharge rate of the biocompatible water-soluble polymer aqueous solution may be 0.5 to 20 ml/hr, preferably 0.7 to 15 ml/hr, and most preferably 1 to 10 ml/hr. Within the above range, it is possible to easily produce a nanofiber having a desired thickness without being broken.

Subsequently, b) coating of a conductive material on the nanofiber mesh sheet may be performed.

Specifically, in the method of producing a nanofiber mesh bioelectrode according to an exemplary embodiment of the present invention, the region of the nanofiber mesh sheet may be partially or entirely coated with a conductive material depending on a design while exposing only a region of the nanofiber mesh sheet to be coated with the conductive material. As a more specific example, a designed shadow mask is placed on the nanofiber mesh sheet, and then a region uncovered with the shadow mask, that is, a region exposed to the outside may be coated with a conductive material. In this case, as described above, the conductive material may be gold (Au), platinum (Pt), silver (Ag), or the like, and may be preferably gold (Au).

In an exemplary embodiment of the present invention, in b), any coating method may be used without particular limitation as long as the conductive material may be coated on the nanofiber mesh sheet by the coating method. Preferably, the coating of the conductive material may be performed by a chemical deposition method or a physical deposition method. As a more specific example, in b), the coating may be performed by a sputtering deposition method, a thermal deposition method, an electron-beam deposition method, a chemical vapor deposition (CVD) method, or an atomic layer deposition (ALD) method.

In addition, the method of producing a nanofiber mesh bioelectrode according to an exemplary embodiment of the present invention may further include coating a protective layer containing a biocompatible hydrophobic polymer on a surface of the nanofiber mesh sheet.

As described above, by forming the protective layer that is insoluble in water on the surface of the nanofiber mesh sheet and then coating the protective layer with the conductive material, the biocompatible water-soluble polymer may not be completely dissolved in water, which may prevent a shape of the nanofiber mesh bioelectrode from being changed greatly. Specifically, when the nanofiber mesh bioelectrode is fixed to skin or a tissue in a living body, adhesion of the nanofiber mesh bioelectrode is performed by partially or entirely dissolving the biocompatible water-soluble polymer through spraying of water. When it is intended to partially dissolve the biocompatible water-soluble polymer so as to maintain the shape of the nanofiber mesh bioelectrode while securing adhesion performance, it is possible to partially dissolve the biocompatible water-soluble polymer by coating the surface of the nanofiber mesh sheet with the protective layer. On the contrary, when it is intended to remove all or almost the biocompatible water-soluble polymer so as to leave only the conductive layer, the protective layer may not be included.

In an exemplary embodiment of the present invention, the protective layer may be coated on the surface of the nanofiber mesh sheet by a typical method. As a specific example, when it is intended to coat the protective layer containing parylene on the surface of the nanofiber mesh sheet, the coating of the protective layer may be performed by a chemical vapor deposition (CVD) method. The protective layer to be coated may have no pinholes and pores because the CVD coating of parylene is performed by vacuum deposition in a form of a gas phase under vacuum. The nanofiber mesh sheet may be stably protected by coating the surface of the nanofiber mesh sheet with parylene due to a very stable molecular structure of parylene. A thickness of a parylene layer may be easily adjusted depending on a deposition time, and thus, the thickness of the protective layer may be adjusted depending on a desired thickness.

In addition, the method of producing a nanofiber mesh bioelectrode according to an exemplary embodiment of the present invention may further include coating an insulating layer containing a biocompatible hydrophobic polymer on a surface of the conductive layer.

As described above, by coating the conductive layer with the biocompatible hydrophobic polymer, a short circuit due to moisture may be prevented, and a short circuit due to a change in shape of the bioelectrode may be prevented. In addition, by forming a pattern on the insulating layer in a state in which the conductive layer is exposed, degradation of sensitivity of the conductive layer may be prevented.

In an exemplary embodiment of the present invention, the insulating layer may be coated on the surface of the conductive layer by a typical method. As a specific example, when it is intended to coat the insulating layer containing parylene on the surface of the conductive layer, the coating of the insulating layer may be performed by a chemical vapor deposition (CVD) method. The insulating layer to be coated may have no pinholes and pores because the CVD coating of parylene is performed by vacuum deposition in a form of a gas phase under vacuum. The conductive layer may be stably protected by coating the surface of the conductive layer with parylene due to a very stable molecular structure of parylene. In addition, a thickness of a parylene layer may be easily adjusted depending on a deposition time, and thus, the thickness of the insulating layer may be adjusted depending on a desired thickness.

Hereinafter, a nanofiber mesh bioelectrode and a method of producing the same according to the present invention will be described in more detail with reference to examples. However, the following examples are only one reference example for describing the present invention in detail, and the present invention is not limited thereto and may be implemented in various forms.

Unless otherwise defined, all technical terms and scientific terms used herein have the same meanings as commonly understood by those skilled in the art to which the present invention pertains. The terms used herein are only for effectively describing a certain example rather than limiting the present invention. Further, unless otherwise stated herein, a unit of an additive may be wt %.

Example 1

1.15 g of polyvinyl alcohol (98 to 99% hydrolyzed, weight average molecular weight: 130,000 g/mol, CAS No. 9002-89-5) was added to 8.85 ml of highly purified water, stirring was performed at 70° C. for 2 hours, and then stirring was performed at room temperature (about 25° C.) overnight, thereby preparing a 11.5 wt % PVA aqueous solution.

The 11.5 wt % PVA aqueous solution was charged into a syringe, and then electrospinning was performed with an electrospinning machine (esprayer ES-2000S, manufactured by Fuence Co., Ltd.). In this case, an inner diameter of a needle of the syringe was 0.31 mm, and a distance between a needle tip of the syringe and a fiber collector was 20 cm. The nanofiber mesh sheet in which nanofibers are entangled in a network form was produced by spinning 500 µl of the PVA aqueous solution at a rate of 4 ml/hr under application of a voltage of 15 kV.

Subsequently, a designed shadow mask was placed on the nanofiber mesh sheet, and gold (Au) was partially deposited on a region of the uncovered nanofiber mesh sheet, thereby producing a nanofiber mesh bioelectrode in which gold was coated on a surface of the nanofiber. In this case, the deposition was performed by a sputtering deposition method, and gold was deposited at a thickness of about 65 nm.

Example 2

A nanofiber mesh bioelectrode was produced in the same manner as that of Example 1, and all processes were performed in the same manner as those of Example 1, except that polyvinylpyrrolidone (weight average molecular weight: 58,000 g/mol, CAS No. 9003-39-8) was used as the biocompatible water-soluble polymer.

Example 3

A nanofiber mesh bioelectrode was produced in the same manner as that of Example 1.

Subsequently, the nanofiber mesh sheet was put into a parylene coating system machine (OBT-PC200, manufactured by Obang technology) to coat a surface of the nanofiber of the nanofiber mesh sheet with parylene. In this case, a thickness of a parylene layer was about 200 nm.

Subsequently, a designed shadow mask was placed on the nanofiber mesh sheet coated with the parylene layer, and gold (Au) was partially deposited on a region of the uncovered nanofiber mesh sheet coated with the parylene layer, thereby producing a nanofiber mesh bioelectrode in which gold was coated on a surface of the parylene layer. In this case, the deposition was performed by a sputtering deposition method, and gold was deposited at a thickness of about 65 nm.

[Result Analysis]

1) Biocompatibility and Discomfort Analysis

In order to confirm biocompatibility and stability of the nanofiber mesh bioelectrode produced by Example 1, water was sprayed to forearm of each of 20 adult participants between ages 22 to 47, and then the nanofiber mesh bioelectrode produced by Example 3 was transferred. A dimension of each sample was 10×10 mm².

Thereafter, the samples were left for 7 days, all samples were removed, and then the forearm was lightly washed with water and dried for 10 minutes.

Subsequently, allergic contact dermatitis and irritant contact dermatitis were evaluated in accordance with a patch test standard by International Contact Dermatitis Research Group (ICDRG). As a result, it was confirmed that itchiness, irritation, asteatosis, erythema, or the like did not appear on the transfer site.

In addition, a degree of discomfort during the patch test period was confirmed through a questionnaire survey of the participants. A visual analog scale (VAS) was used as the degree of discomfort, and the degree of discomfort was evaluated on a 0 to 10 scale (0: not uncomfortable at all, 10: very uncomfortable). As a result, it could be confirmed that in the case of the nanofiber mesh bioelectrode produced by Example 1, an average of the degrees of discomfort was 1.16, and the participants did not feel discomfort to the extent that attachment of the bioelectrode was not recognized.

2) Electrical Property Analysis

In order to measure a conductance of the nanofiber mesh bioelectrode, water was sprayed onto a polyimide substrate, and then the nanofiber mesh bioelectrode of Example 1 was transferred.

The electrical property was evaluated with a digital multimeter, and a resistance (p) of a nano mesh was calculated by the following Equation 1.

$$\rho = R \times \frac{A \times x}{L} \quad \text{[Equation 1]}$$

In Equation 1, R represents a resistance, A represents a cross-sectional area, x represents an application range of a Au layer, and L represents a length of the Au layer. In this case, the cross-sectional area A is obtained by multiplying the width of the Au layer by a thickness of the Au layer. The thickness of the Au layer was 65 nm. The application range of the Au layer obtained by an SEM image was 36%. However, the above calculation may be based on the assumption that all nanomeshes are electrically connected to each other.

Figure 4A:
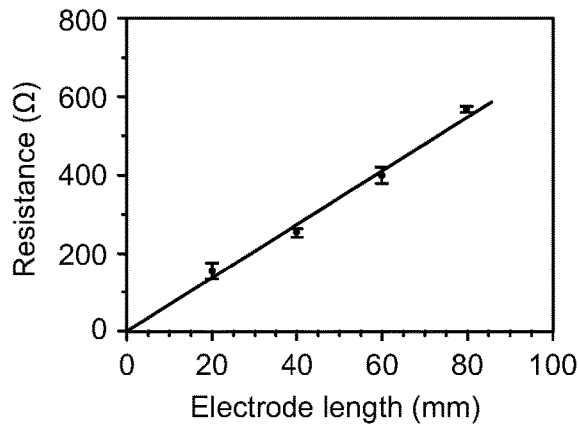
FIGS. 4A and 4B illustrate results of an electrical property test according to changes in width and length of a Au layer constituting the nanofiber mesh bioelectrode.
Figure 4B:
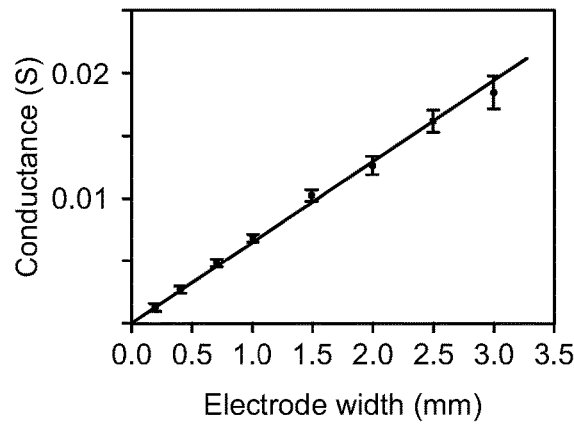

As a result, it could be confirmed that the resistance was increased as the length of the Au layer was increased as illustrated in FIG. 4A, and the conductance was increased as the width of the Au layer was increased as illustrated in FIG. 4B.

3) Electrical Property and Mechanical Property Analysis

In order to evaluate stretchability of the nanofiber mesh bioelectrode, a polyurethane sheet pre-stretched by 15% having a thickness of 20 μm was used as a substrate. Water was sprayed to the polyurethane sheet, and then the nanofiber mesh bioelectrode was transferred. When the pre-stretched polyurethane sheet was released, the nanofiber mesh bioelectrode also contracted together with the polyurethane sheet. A length of the contracted nanofiber mesh bioelectrode was set as an "initial value".

Figure 5A:
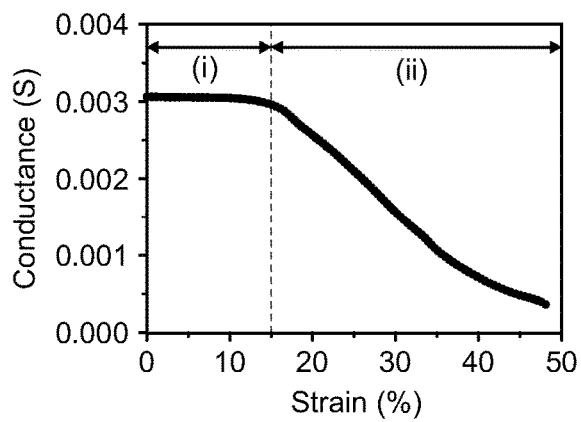
FIG. 5A illustrates data of a conductance test according to a strain of a nanofiber mesh bioelectrode produced according to an exemplary embodiment of the present invention.

Next, the polyurethane sheet onto which the nanofiber mesh bioelectrode was transferred was fixed to an upper portion and a lower portion of a tensile tester (AG-X, manufactured by Shimadzu Corporation), and then stretchability thereof was evaluated. In order to prevent damage of the nanofiber mesh bioelectrode and to ensure the conductance of the nanofiber mesh bioelectrode, an anisotropic conductive film (manufactured by Shin-Etsu Polymer Co., Ltd.) was placed between an upper portion of the polyurethane sheet onto which the nanofiber mesh bioelectrode was transferred and a clamp of the tensile tester. As illustrated in FIG. 5A, a conductance (S) was hardly reduced up to a 15% strain, and the conductance began to be significantly reduced when the strain was 20% or more.

Figure 5B:
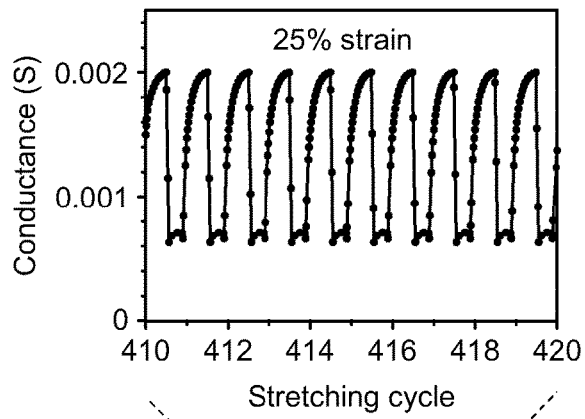
FIGS. 5B and 5C illustrate results of the conductance test according to periodical stretching and contracting of a nanofiber mesh bioelectrode produced according to an exemplary embodiment of the present invention.
Figure 5C:
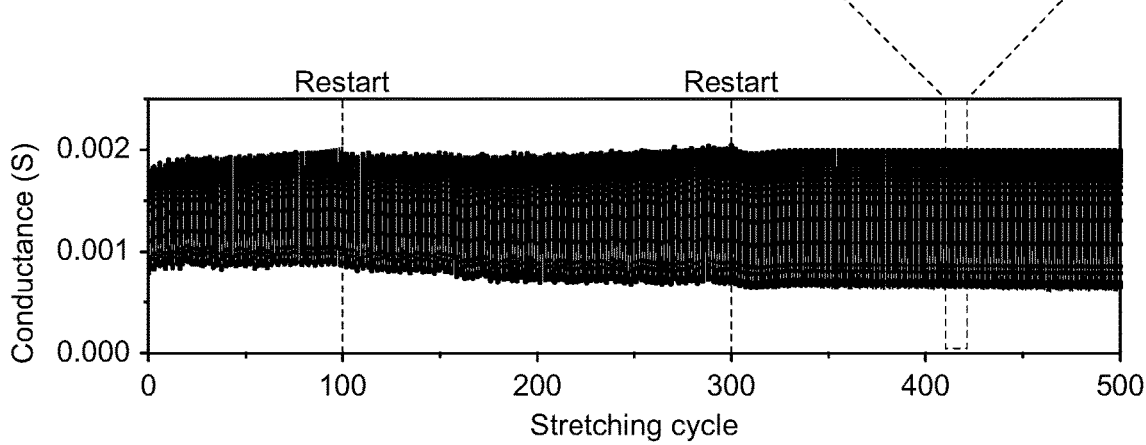

FIGS. 5B and 5C illustrate the results of a periodic strain test. One stretching cycle was set as follows: a 25% strain was applied for 1 second, the operation was suspended for 1 second, the nanofiber mesh bioelectrode contracted again to the original state for 1 second, and finally, the operation was suspended for 1 second. The test was carried out by performing 500 stretching cycles.

As illustrated in FIGS. 5B and 5C, it could be appreciated that the conductance was rapidly changed during stretching of the bioelectrode, and was gradually recovered to the initial value during contraction of the bioelectrode. The conductance was not significantly changed even when the number of times of stretching was increased to 500.

By using a polymer having excellent biocompatibility and a conductive material, the nanofiber mesh bioelectrode according to the present invention may have excellent biocompatibility. Further, by having the nanofiber mesh structure in which fiber strands are entangled in a network form, the nanofiber mesh bioelectrode according to the present invention may have excellent permeability to moisture and air. Therefore, the nanofiber mesh bioelectrode may not cause dermatitis, damage to a nerve tissue, and the like even when the nanofiber mesh bioelectrode is attached to skin or is implanted in a living body for a long period of time.

In addition, the nanofiber mesh bioelectrode according to the present invention has the nanofiber mesh structure in which fiber strands are entangled in a network form, such that the nanofiber mesh bioelectrode may have excellent flexibility similar to that of skin. Therefore, the nanofiber mesh bioelectrode may be easily fixed to skin or to a tissue in a living body, and may not be easily detached from the tissue because it is flexibly bent or stretched even when a human body moves. Thus, as the nanofiber mesh bioelectrode is not easily detached from the tissue for a long period of time, the nanofiber mesh bioelectrode may easily measure a biosignal or may easily apply electrical stimulation for a long period of time.

In addition, since the biocompatible water-soluble polymer serves as an adhesive, the nanofiber mesh bioelectrode may be attached and fixed to skin or a tissue in a living body without a separate adhesive material.

In addition, in the method of producing a nanofiber mesh bioelectrode according to the present invention, the nanofiber mesh bioelectrode is produced by producing the nanofiber mesh sheet in which the nanofibers are entangled in a network form by using electrospinning in advance, and then coating the nanofiber mesh sheet with the conductive material, such that a microelectrode may be relatively easily produced due to easy micromachining.

Hereinabove, although the present invention has been described by specific matters and limited exemplary embodiments, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to these exemplary embodiments, but the claims and all of modifications equal or equivalent to the claims are intended to fall within the spirit of the present invention.

What is claimed is:

1. A nanofiber mesh bioelectrode comprising:
   a nanofiber mesh sheet in which nanofibers are entangled in a network form, the nanofibers comprising a biocompatible water-soluble polymer; and
   a conductive layer coated on the nanofiber mesh sheet and including a conductive material.

2. The nanofiber mesh bioelectrode of claim 1, further comprising a protective layer formed between the nanofiber mesh sheet and the conductive layer and containing a biocompatible hydrophobic polymer.

3. The nanofiber mesh bioelectrode of claim 2, wherein the biocompatible hydrophobic polymer is one or two or more selected from the group consisting of parylene, polycaprolactone (PCL), polylactic acid (PLA), and a polylactic acid-co-glycolic acid (PLGA) copolymer.

4. The nanofiber mesh bioelectrode of claim 2, wherein a thickness of the protective layer is 50 to 1,000 nm.

5. The nanofiber mesh bioelectrode of claim 1, wherein the biocompatible water-soluble polymer is one or two or more selected from the group consisting of polyvinyl alcohol (PVA), polyethylene glycol (PEG), polypropylene glycol (PPG), polyacrylic acid (PAA), carboxymethyl cellulose (CMC), polyvinylpyrrolidone (PVP), starch, gelatin, hyaluronic acid, chi tin, chi tosan, alginic acid, dextran, fibrin, heparin, and salts thereof.

6. The nanofiber mesh bioelectrode of claim 1, wherein a thickness of the nanofiber is 10 to 990 nm.

7. The nanofiber mesh bioelectrode of claim 1, wherein a thickness of the conductive layer is 1 to 500 nm.

8. The nanofiber mesh bioelectrode of claim 1, wherein the nanofiber mesh bioelectrode is an implantable bioelectrode.

9. The nanofiber mesh bioelectrode of claim 1, further comprising an insulating layer formed on the conductive layer and containing a biocompatible hydrophobic polymer.

10. The nanofiber mesh bioelectrode of claim 9, wherein the insulating layer is a patterned insulating layer having a pattern in which the conductive layer is exposed to an upper portion of the insulating layer.

11. A method of producing a nanofiber mesh bioelectrode, comprising:
   a) producing a nanofiber mesh sheet in which nanofibers are entangled in a network form by using electrospinning, the nanofibers comprising a biocompatible water-soluble polymer; and b) coating a conductive material on the nanofiber mesh sheet.

12. The method of claim 11, further comprising, before the coating of the conductive material, coating a protective layer containing a biocompatible hydrophobic polymer on the nanofiber mesh sheet.

13. The method of claim 12, wherein the coating of the protective layer is performed by a chemical vapor deposition (CVD) method.

14. The method of claim 11, wherein, in b), the coating is performed by a sputtering deposition method, a thermal deposition method, an electron-beam deposition method, a chemical vapor deposition (CVD) method, or an atomic layer deposition (ALD) method.

* * * * *